United States Patent [19]
King, Jr.

[11] 3,965,729
[45] June 29, 1976

[54] LOAD CRACK TESTING DEVICE

[75] Inventor: William E. King, Jr., Bowie, Md.

[73] Assignee: The United States of America as represented by the Secretary of the Navy, Washington, D.C.

[22] Filed: Oct. 1, 1975

[21] Appl. No.: 618,727

[52] U.S. Cl. ............................ 73/90; 73/103
[51] Int. Cl.² ............................ G01N 3/10
[58] Field of Search ............ 73/100, 90, 93, 97, 73/103

[56] References Cited
UNITED STATES PATENTS

| | | | |
|---|---|---|---|
| 1,825,954 | 10/1931 | Hansard et al. | 73/100 |
| 2,277,813 | 3/1942 | Bernhard | 73/93 |
| 3,380,289 | 4/1968 | Walters et al. | 73/103 X |

*Primary Examiner*—Jerry W. Myracle
*Attorney, Agent, or Firm*—R. S. Sciascia; Philip Schneider; Melvin L. Crane

[57] ABSTRACT

A sustained constant load cantilever loading type specimen testing machine. The machine includes a rigid grip which grips one end of a specimen. The other end of the specimen is secured rigidly to a cantilever. A hydraulic piston is connected to the cantilever and operated by a hydraulic pump. The load is measured by a calibrated load cell. Auxiliary equipment such as an electrical timer, control switches and safety switches are used for operation of the system.

4 Claims, 3 Drawing Figures

3,965,729

LOAD CRACK TESTING DEVICE

BACKGROUND OF THE INVENTION

This invention relates to devices for testing metals and more particularly to a sustained constant-load crack testing device for determining the critical stress intensity threshold for stress-corrosion cracking $K_{Iscc}$ or sustained load cracking $K_{Islc}$ of high strength metals.

Heretofore, tension-compression testing machines have been used for testing metals such as disclosed in U.S. Pat. Nos. 3,194,062 and 3,273,383. Simple large space consuming devices have been used which employ weights suspended at the end of a bar clamped to a specimen. Using weights, require large storage areas, large test racks, and only tension can be applied to a sample. The patented devices listed are for small samples and can be used for both tension and compression testing.

SUMMARY OF THE INVENTION

This invention employs a stationary base for rigidly clamping one end of a sample in place with a hydraulically controlled arm connected to the opposite end of the specimen. A metering valve in combination with an overload pressure relief valve cooperate to apply a constant load on the test sample. The load is measured by the use of a standard strain-type load cell which load is indicated or recorded by the use of a digital voltmeter or any other suitable device to indicate load cell output.

It is therefore an object of this invention to provide a testing device for large samples which require a relatively small space, yet has a high load capacity.

Another object is to provide a strain testing device which has capability of both tension and compression testing.

DETAILED DESCRIPTION

Figure 1:
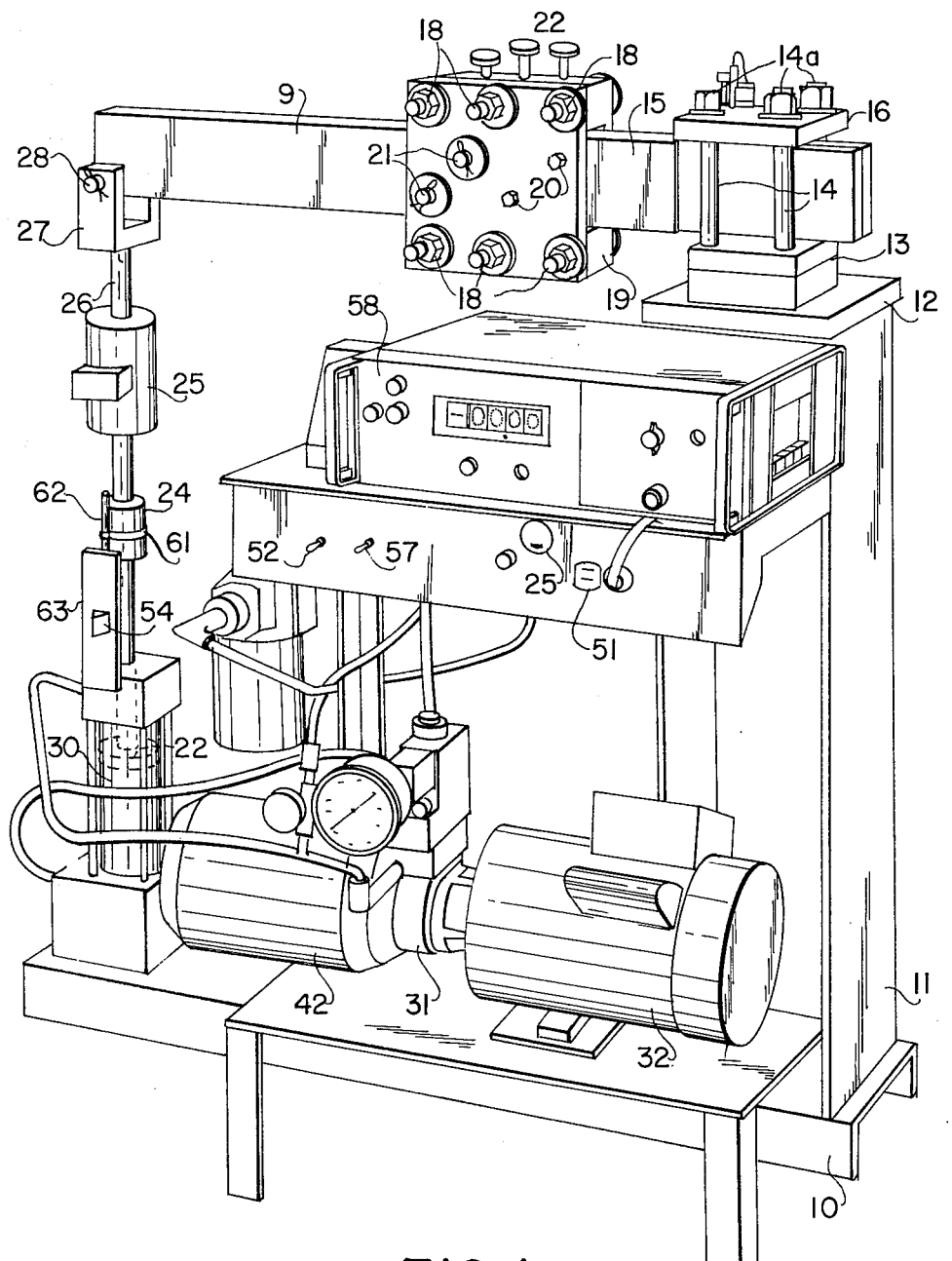
FIG. 1 illustrates a perspective view of the device illustrating the relative parts.
Figure 2:
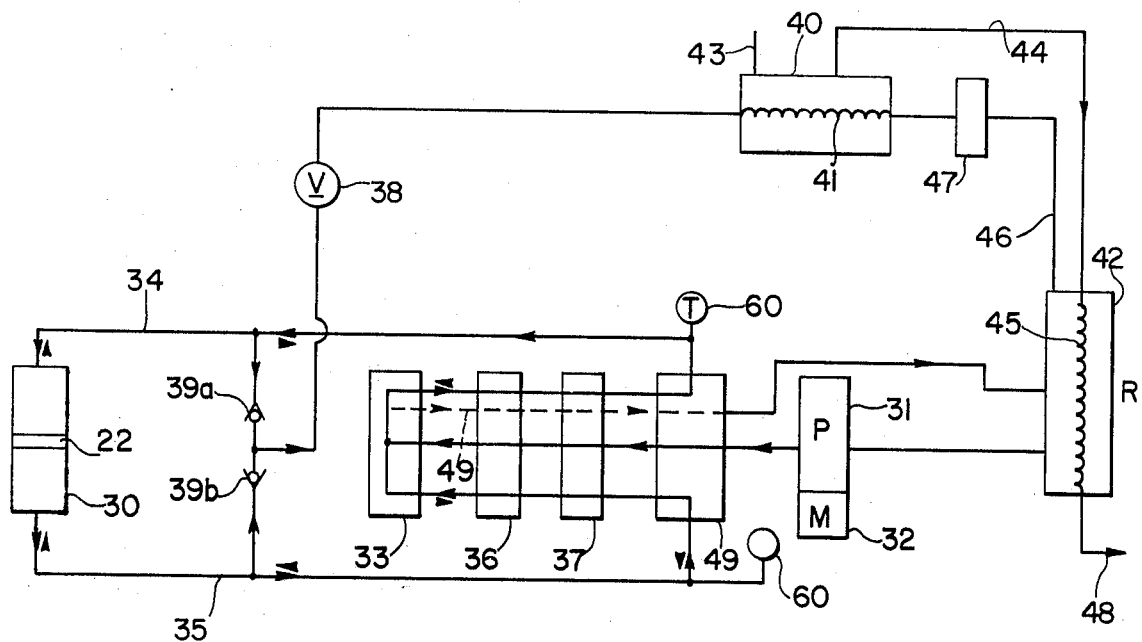
FIG. 2 illustrates a block diagram of the hydraulic system.

Now referring to the drawing wherein like reference characters refer to like parts, there is shown by illustration a metals testing device made in accordance with the teachings of this invention. The testing machine includes a supporting base 10 to which an I-beam 11 is welded at the bottom in an upright position normal to the base. A plate 12 welded to the upper end of the I-beam supports a rigid clamping means. The clamping means includes a base 13 with four equally spaced upright bolts 14 each having a threaded end on which suitable nuts 14a are threaded. The test bar 15 is secured at one end by a plate 16 which fits onto the bolts 14 above the upper surface of the test bar. The other end of the test bar is secured by spaced plates 17 bolted together by bolts 18 passing through appropriate spacer bars 19 one above and one below the test bar and positioned between the plates 17. An extension arm 9 is secured in place between the plates 17 by hardened pins 21 and also held in place by bolts 18 as described for the adjacent end of the test bar. Bolts 20 are used above and on the side of the test bar in order to adjust clamping alignment. Strain is applied to the test bar by use of a cylinder 30 which contains a hydraulically operated piston 22 therein whose rod 23 is secured to a coupling 24 that secures one end of a load measuring standard strain gage-type load cell 25 in place. The opposite end of the strain gage-type load cell 25 is connected by a rod 26 to a clevis 27 that is secured to the arm extension 9 by a hardened pin that passes through the clevis and the arm extension.

A variable delivery hydraulic pump 31 such as a PVTM No. DO5ASIL driven by a motor 32 such as a PVTM No. CF685319 applies a hydraulic fluid force on either side of the piston 22 which in turn applies a force on the extension arm 9 and test bar 16. A fluid reversing-neutral position electrically controlled valve 33 such as a Parker directional control valve PVY16D1 is used to reverse the fluid flow so that the hydraulic pressure may be applied to the top of the piston through feed line 34 to apply a stress on the test bar or through feed line 35 to apply a pressure on the bottom of the piston to apply a compression force on the test bar. The fluid pressure is controlled by use of a fluid flow control valve 36 such as a Parker MF-200-S-11 and a pressure relief valve 37 such as a Parker MPR-200-S-2. The fluid from the pump flow control valve and pressure relief valve is directed to the fluid directional valve 33 and then through the subplate 49 and the proper pressure line to the piston 22. The fluid directional valve has three settings, one setting applies pressure from the pump to the upper surface of the piston for stress testing, one setting applies the fluid under pressure to the bottom of the piston for compression testing and the third is a neutral setting. In the neutral setting position, the pressure is the same on each surface of the piston for no movement of the piston. Each of the pressure-return lines 34 and 35 to the piston cylinder are connected by a common line including one way check valves 39a and 39b therein with a line including a bypass needling valve 38 which permits fine tuning of the pressure in the pressure line. The bypass needling valve is used to accurately adjust the desired pressure on the desired piston face such that the correct pressure is applied to the test bar through the piston movement. The fluid bypassed by the bypass valve is directed through a heat exchanger 40 that includes a cooling spiral 41 for cooling the hydraulic fluid prior to returning to the reservoir 42, cooling water is admitted to the heat exchange 40 through the inlet line 43 and the water flows from the heat exchanger through outlet line 44 which is appropriately connected to a cooling spiral element 45 in the reservoir. The hydraulic fluid line 46 from the heat exchanger to the reservoir includes therein a filter 47 to filter any particles that may be in the hydraulic fluid. The coolant fluid from the exchanger spiral 45 in the reservoir is connected to a waste line 48 if not in a closed circuit or to a coolant means if in a closed coolant cycle. The fluid is filtered in the bypass line so that the fluid pressure through the filter will be at the least pressure to provide good filtering of the fluid thereby not requiring a high pressure filter body. Check valves 39 control the fluid flow direction to the metering valve 38 and the bypass line through the heat exchanger to the reservoir.

In order to conserve space, a subplate 49 is secured to the pump, and the relief valve 36, flow control valve 37, and directional control valve 33 are closely stacked upon the subplate and fluid flow is controlled through the subplate. A subplate such as a Parker No. 695751 is an element which receives fluid under pressure from the pump and is provided with passages therein with appropriate outlet and inlet connections which connect with the appropriate valves with interconnecting passages within the subplate to direct the fluid to or from the proper element as shown by the block diagram. The dotted line 49 represents the return line from the direction control valve 33 to the reservoir through the subplate. Pressure indicators 60 are connected with each pressure-return line 34, 35 to indicate the pressure of the fluid.

Figure 3:
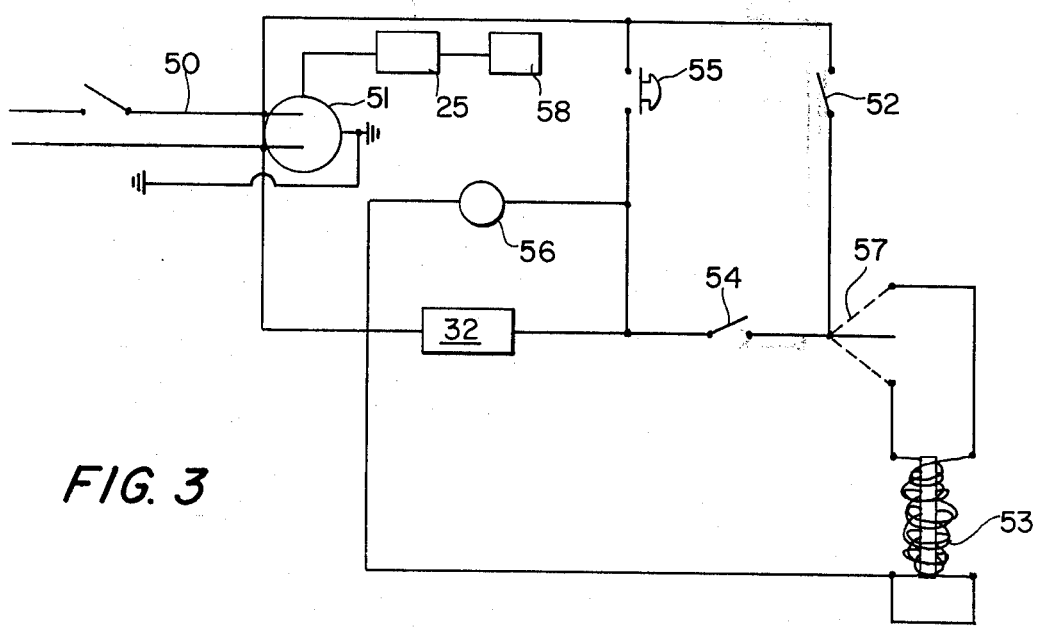
FIG. 3 illustrates a schematic diagram of the electrical system.

FIG. 3 illustrates the electrical control circuitry for controlling the electrical elements of the test system. The electrical controls include the main line 50 which connects with a 115 volt 20 amp source including a main switch 51. An output 51 for connecting any desired extension such as the digital voltmeter 58 that indicates or records the strain load on the test bar from the load cell 25. The circuitry includes a switch 52 which controls the electrical power through a three position switch 57 to the solenoid 53 that controls the directional control valve 33 and supplies the power to the motor 32. The three position switch has an up, down, and neutral position corresponding to up, down, and neutral actions on the cylinder. A reset timer 56 is electrically connected across the motor circuit in order to record the time of specimen failure and a contact switch 54 in series with the motor turns off motor power at the time of failure. A push-button switch 55 is also provided for controlling the motor independent of the contact switch 54.

During test, it is desirous that the load be brought to the desired level and maintained at that load for as long a period as desired. Therefore, prior to the first use, subsequent to loading of the first test specimen, the system should be "flushed" i.e. operated with the hydraulic fluid flowing through the metering valve 38 to the filter 47 so that any foreign particles in the system may be filtered out of the fluid prior to fine tuning of the hydraulic system for testing.

In operation for applying stress onto a test bar, the test bar is assembled in place, with contact switch 54 closed and metering valve 38 open, the main electrical switch 49 and then switch 52 are closed and the electrical switch 57 for the fluid directional control valve 33 is positioned so that fluid under pressure flows through pressure line 34 to the upper side of the piston. Thus, the piston will be forced downwardly to apply a stress on the sample. The pump forces the hydraulic fluid into the subplate 49, through the relief valve 36, on to the flow control valve 37 which is adjusted at the desired load speed. The pressure relief valve operates to pass fluid that is above the desired pressure through an internal return line in the valve stack back to the reservoir 42. Fluid under pressure to be used passes from the relief valve 36 through the fluid direction control valve 33 back to the subplate via one of two internal pressure paths in the valve stack, then from the subplate through pressure line 34 to the upper side of the piston in cylinder 30. The fine tuning pressure (bypass) valve 38 connected with pressure lines 34–35 is provided to aid in correcting or fine tuning the fluid pressure on the piston. The fluid to the fine tuning valve 38 passes through a check valve 39a and is blocked by check valve 39b and directed through valve 38 to a fluid coolant tank which cools the fluid as it passes through the tank. The by-pass fluid from the cooling tank passes through the filter 47 and through the filter 47 and through return line 46 back to the reservoir 42. The coolant water also passes from the coolant tank to a coil in reservoir 42 to further cool the fluid in the reservoir. A pressure indicator is connected with the pressure line through the subplate to indicate the pressure of operation. The metering valve 38 is closed or opened a little for passage of more or less fluid in order to obtain and retain a more accurate load speed. Once the system has been brought up to the proper pressure the metering valve is adjusted to make any minor corrections, if necessary. Fluid in the non-pressure line 35 will return to the reservoir through the control valve 33 and the return line through subplate 49.

For compression testing, the system is operated the same as above described with the exception of switch 57 which is properly switched to operate the fluid direction control valve to apply fluid under pressure to the bottom of the piston through line 35 rather than onto the upper surface thereof through line 34. The fine tuning valve 38 will also bypass fluid for the desired load through check valve 39b.

It is noted that a timer is electrically connected across the motor. The timer operates when the motor operates in order to provide a record of the time during which a test is conducted.

The coupling 24 is provided with a bracket 61 with a rod 62 attached thereto. The rod 62 parallels the piston rod and operates switch 54 held by bracket 63 in order to break the circuit to the motor and timer when the specimen breaks. Therefore the time of operation may be determined even though the specimen may break during the night, on weekends, or any other time that an operator is not at the test device.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A sustained constant load cantilever loading type specimen testing system; which comprises
   a support
   means on said support for anchoring one end of a test specimen in place,
   a cantilever
   means for securing one end of said cantilever and the unanchored end of said test specimen rigidly together in linear alignment,
   a hydraulic pressure cylinder containing a piston therein,
   means for connecting said piston with the free end of said cantilever,
   a hydraulic fluid reservoir
   a hydraulic pump means connected to receive fluid from said reservoir,
   a motor for driving said hydraulic pump to supply hydraulic fluid under pressure to said cylinder,
   a subplate with interconnected stacked valves connected therewith
   said valves including in succession a relief valve, a flow control valve and a directional fluid flow valve,
   said subplate and said stacked valves including sufficient interconnecting fluid pressure lines therethrough to control fluid flow under pressure from said hydraulic pump through said relief valve, said flow control valve and said directional fluid flow valve to said cylinder and sufficient interconnecting return lines to return fluid from said pressure relief valve and said directional flow valve to said reservoir, and a load indicating means for determining stress or strain on said test specimen.

2. A sustained constant load specimen testing system as claimed in claim 1; which comprises, a metering valve connected to said lines between said cylinder and said directional fluid flow valve in order to fine tune the force-load applied onto said test specimen.

3. A sustained constant load specimen testing system as claimed in claim 2; in which said load indicating means is a strain-gauge type load cell connected between said piston and the free end of said cantilever, and an indicator electrically connected with said strain-gauge type load cell for indicating the load on said specimen.

4. A sustained constant load specimen testing system as claimed in claim 2; which includes, a water coolant system for cooling the fluid in said testing system.

* * * * *